United States Patent
Bosch

(10) Patent No.: US 12,115,079 B2
(45) Date of Patent: Oct. 15, 2024

(54) HIP JOINT TETHER DEVICE

(71) Applicant: University of Pittsburgh—Of the Commonwealth System of Higher Education, Pittsburgh, PA (US)

(72) Inventor: Patrick Peter Bosch, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 433 days.

(21) Appl. No.: 17/600,259

(22) PCT Filed: Apr. 15, 2020

(86) PCT No.: PCT/US2020/028346
§ 371 (c)(1),
(2) Date: Sep. 30, 2021

(87) PCT Pub. No.: WO2020/214726
PCT Pub. Date: Oct. 22, 2020

(65) Prior Publication Data
US 2022/0160511 A1    May 26, 2022

Related U.S. Application Data

(60) Provisional application No. 62/835,362, filed on Apr. 17, 2019.

(51) Int. Cl.
| A61F 2/36 | (2006.01) |
| A61F 2/32 | (2006.01) |
| A61F 2/30 | (2006.01) |

(52) U.S. Cl.
CPC .............. *A61F 2/3609* (2013.01); *A61F 2/32* (2013.01); *A61F 2002/30062* (2013.01);
(Continued)

(58) Field of Classification Search
CPC .. A61F 2/32; A61F 2/3609; A61F 2002/3233; A61F 2002/30566;
(Continued)

(56) References Cited

U.S. PATENT DOCUMENTS

| 2,397,545 A | 4/1946 | Hardinge |
| 7,172,595 B1 | 2/2007 | Goble |

(Continued)

OTHER PUBLICATIONS

International Search Report and Written Opinion for related International Application No. PCT/US2020/028346, 11 pages, mailed Jul. 1, 2020.

*Primary Examiner* — Dinah Baria
(74) *Attorney, Agent, or Firm* — Klarquist Sparkman, LLP

(57) ABSTRACT

Hip tethering devices comprise a femoral implant including a housing that anchors the femoral implant to the femur, at least one spring, and a slider, such that the slider can move relative to the housing via compression and expansion of the at least one spring. A tether has a first end that anchors to the acetabulum, the tether passes through the femoral head, and a second end couples to the slider of the femoral implant, such that the tether spans across the patient's hip joint and relative motion between the slider and the housing allows a limited degree of separation of the femoral head from the acetabulum, while the at least one spring applies a variable tension load to the tether that resists separation of the femoral head from the acetabulum.

19 Claims, 7 Drawing Sheets

(52) U.S. Cl.
CPC .............. *A61F 2002/30462* (2013.01); *A61F 2002/30566* (2013.01); *A61F 2002/3233* (2013.01)

(58) Field of Classification Search
CPC ........... A61F 2002/30462; A61B 17/58; A61B 17/86; A61B 17/746; A61B 17/74; A61B 2017/681
See application file for complete search history.

(56) References Cited

U.S. PATENT DOCUMENTS

| | | | |
|---|---|---|---|
| 2010/0063503 A1 | 3/2010 | Dell'Oca | |
| 2010/0298834 A1 | 11/2010 | Hildebrandt | |
| 2012/0130492 A1* | 5/2012 | Eggli | A61F 2/0811 623/13.14 |
| 2014/0336760 A1* | 11/2014 | Eggli | A61F 2/0811 623/13.14 |

* cited by examiner

HIP JOINT TETHER DEVICE

CROSS-REFERENCE TO RELATED APPLICATIONS

This application is the U.S. National Stage of International Application No. PCT/US2020/028346, filed Apr. 15, 2020, which claims the benefit of U.S. Provisional Application No. 62/835,362 filed Apr. 17, 2019, which is incorporated by reference herein in its entirety.

FIELD

This disclosure is related to treatment of the abnormal hip joint conditions via hip joint stabilization.

BACKGROUND

Developmental dysplasia of the hip (DDH) is the incorrect development of the hip joint. If a hip does not seat properly early in life, it will not develop properly. Persistence of hip dysplasia into adolescence and adulthood may result in abnormal gait, decreased strength and increased rate of degenerative hip and knee joint diseases. Approximately 1 out of 6 newborns will have some type of hip instability and 2-3 out of every 1,000 infants will require surgical treatment. Despite efforts to recognize and treat all cases of DDH soon after birth, diagnosis is delayed in some children, and outcomes deteriorate with increasing delay of presentation.

In complex cases where DDH is not treatable with closed reduction techniques or in late diagnosed cases (beyond 18 months) or in Cerebral Palsy or Spina Bifida where neuromuscular hip dislocations are common, additional open reduction surgeries and hip reconstruction surgeries can be a necessity. Current surgical techniques involve removing impediments to hip reduction. Complete or partial re-dislocations (subluxations) occur in even expert hands. Failed reductions lead to additional surgical procedures, prolonged immobilization and suboptimal outcomes.

There is an unmet need for a more reliable hip reduction surgery that could help to increase success in restoring normal anatomy and function. In the case of neuromuscular hips, many are even not treated (termed "benign neglect") because of high failure rates with current surgical practice. A more reliable method could substantially increase indications for treatment. In developing countries that have high rates of late presenting or neglected hip dislocations, they remain a significant cause of hip arthritis and disability. A reliable hip tether device and technique can also be applied to routine DDH cases to improve success, decrease immobilization, and decrease residual dysplasia and limit the need for late reconstructive surgery. It may also shorten days of stay at the hospital and costs of secondary reconstruction surgeries. Currently, hospital costs for DDH patients undergoing surgical reconstruction of the hip are very high and additional reconstruction surgeries owing to failed primary surgeries incur additional costs.

SUMMARY

Disclosed herein are devices and methods that dynamically stabilize the hip, such as in patients with dysplasia who must undergo an open surgical procedure, where, post-operatively, natural movement promoting healing and redevelopment is allowed. Disclosed herein is a tethering device that includes a tether that has one end anchored in or behind the acetabulum and is tunneled through the femoral head where a second end is secured to an implanted device in or near the lateral cortex of the greater trochanter region. The disclosed tethering device can reproduce a dynamic stabilization of the hip joint and can also enable the displaced hip to stabilize, simulating the original anatomical functionality. Although the disclosed embodiments are focused on hips, the disclosed suture-anchor type implant device, or similar devices, can also be applied in other locations and to solve other problems, such as traumatic hip and shoulders and total joint tissues.

An exemplary hip tethering device comprises a femoral implant including a housing that anchors the femoral implant to the femur near the greater trochanter region, at least one spring coupled to the housing, and a slider coupled to the at least one spring, such that the slider can move relative to the housing via compression and expansion of the at least one spring. The exemplary hip tethering device further comprises a tether having a first end and a second end, wherein the first end anchors at or near a patient's acetabulum, the tether passes through the patient's femoral head, and the second end couples to the slider of the femoral implant, such that the tether spans across the patient's hip joint and relative motion between the slider and the housing allows a limited degree of separation of the femoral head from the acetabulum, while the at least one spring applies a variable tension load to the tether that resists separation of the femoral head from the acetabulum. In some embodiments, the femoral implant comprises a primary spring and a secondary spring, wherein the primary spring is always engaged between the housing and the slider, and wherein the secondary spring is only engaged between the housing and the slider when the primary spring is compressed at least a predetermined distance.

Exemplary methods of implanting a dynamic hip tethering device can comprise anchoring a first end of a tether at or near a patient's acetabulum, implanting a femoral implant is the patient's femur adjacent its femoral head, and passing the tether through the femoral implant and coupling a second end of the tether to a slider of the femoral implant, such that the tether spans across the patient's hip joint, and wherein the slider is coupled to a spring of the femoral implant such that the slider can move relative to a housing of the femoral implant that is engaged with the femur.

After implantation, methods can include inducing relative motion between the slider and the housing to cause minor separation of the patient's femoral head from the acetabulum while the spring compresses and applies a tension load to the tether that resists separation of the femur head from the acetabulum. In some methods, the tether is implanted such that the tether is under a first non-zero tension when the patient's hip joint is not separated, such that the first non-zero tension resists separation of the hip joint, and wherein the slider is configured to travel a maximum distance relative to the housing to allow the femur head to separate the maximum distance from the acetabulum, and wherein when the hip joint is separated the maximum distance the tether is under a second non-zero tension that is greater than the first non-zero tension.

In some methods, implanting the femoral implant comprises implanting the formal implant in a greater trochanter region of the femur. In some methods, anchoring the first end of the tether comprises passing the tether through an opening in the acetabulum. In some methods, coupling the second end of the tether to the slider comprises passing the tether through the slider and securing the second end of the tether to a button or washer positioned behind the slider within the housing. Some methods comprise attaching a cover to the housing that covers the slider, such that the slider and the second end of the tether are contained inside the housing. In some methods, implanting the femoral implant comprises rotating the housing such that threads on the housing engage with the femur. Some methods comprise implanting a metal plate that is attached to an outer surface of the femur, wherein the housing of the femoral implant is secured to or integrated with the metal plate and implanted during a common procedure. Some methods comprise re-tensioning the tether after an initial implantation procedure to adjust tension in the tether.

The foregoing and other objects, features, and advantages of the disclosed technology will become more apparent from the following detailed description, which proceeds with reference to the accompanying figures.

DETAILED DESCRIPTION

Disclosed herein are devices and methods for dynamically stabilizing a patient's hip joint, while allowing for a functional degree of separation/displacement between the femur head and the hip socket. A spring-loaded implant in the femur is coupled to a tether spanning from the femur head to the hip socket. The implant uses a variable spring force to apply tension to the tether that restricts the femur head from moving too far out of the socket. As the femur head moves farther away from the tether anchor location in the hip socket, the spring compresses and applies an increasing large tension force on the tether, which urges the femur head back into the proper position in the socket. The spring also provides some degree of give in case an unexpectedly strong force is applied to joint, which could otherwise snap the tether. In some embodiments, a compound spring or multiple springs can be used to generate a more complex tension profiles as a function of hip displacement. The tether and hip anchor can be dissolvable/bio-resorbable after a desired about of time, and the device implanted in the femur can be later removed.

Figure 1:
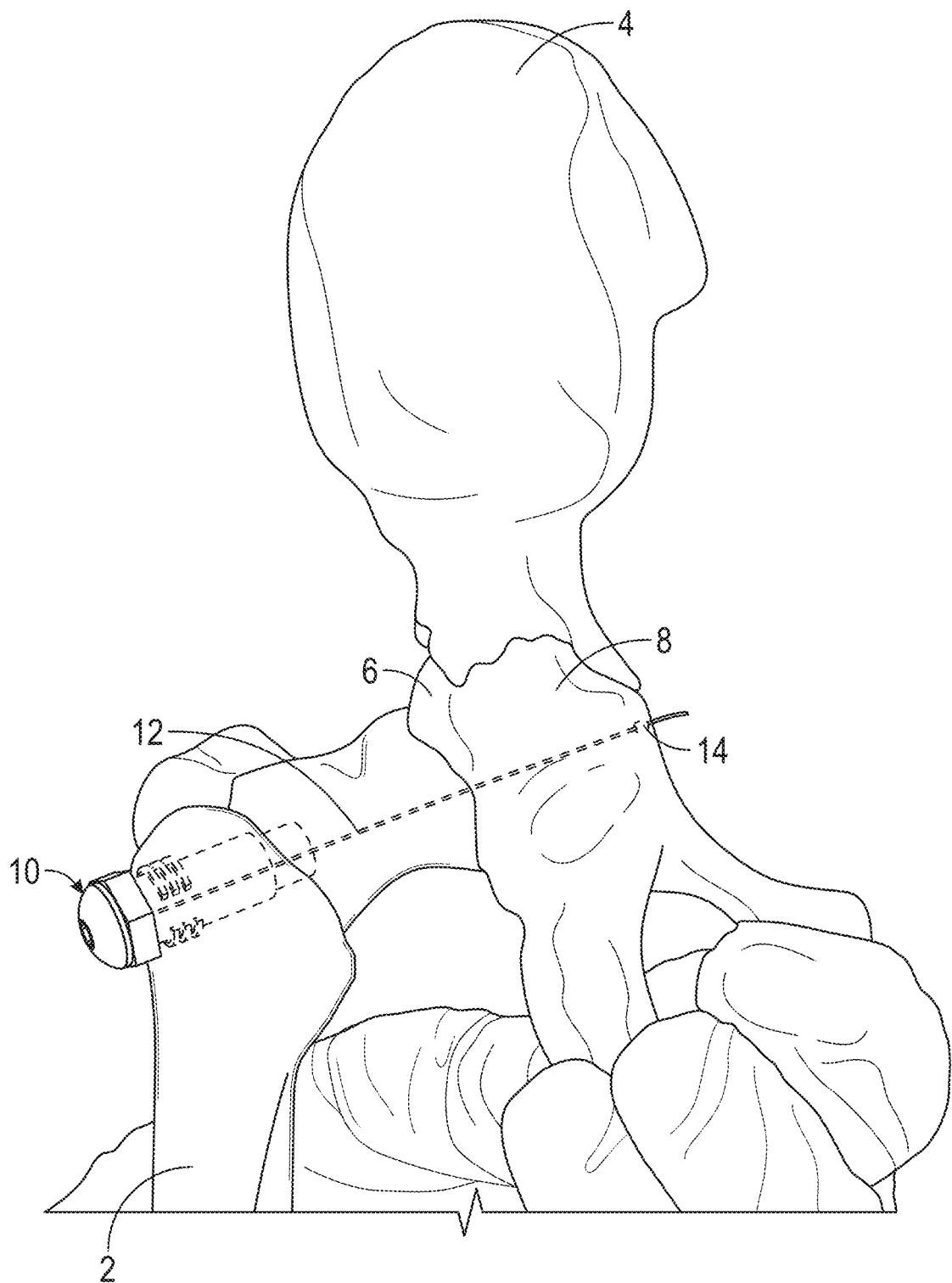
FIG. 1 shows an exemplary hip joint tether device.

FIG. 1 shows a hip model with an exemplary hip joint tether device implanted. The device 10 is implanted in the area of the greater trochanter of the femur 2, in a cavity that is surgically formed using a drill, etc. The tether 12 passes through a tunnel in the femoral head 6 and is anchored into the hip bone 4 in the area of the acetabulum 8.

Figure 2:
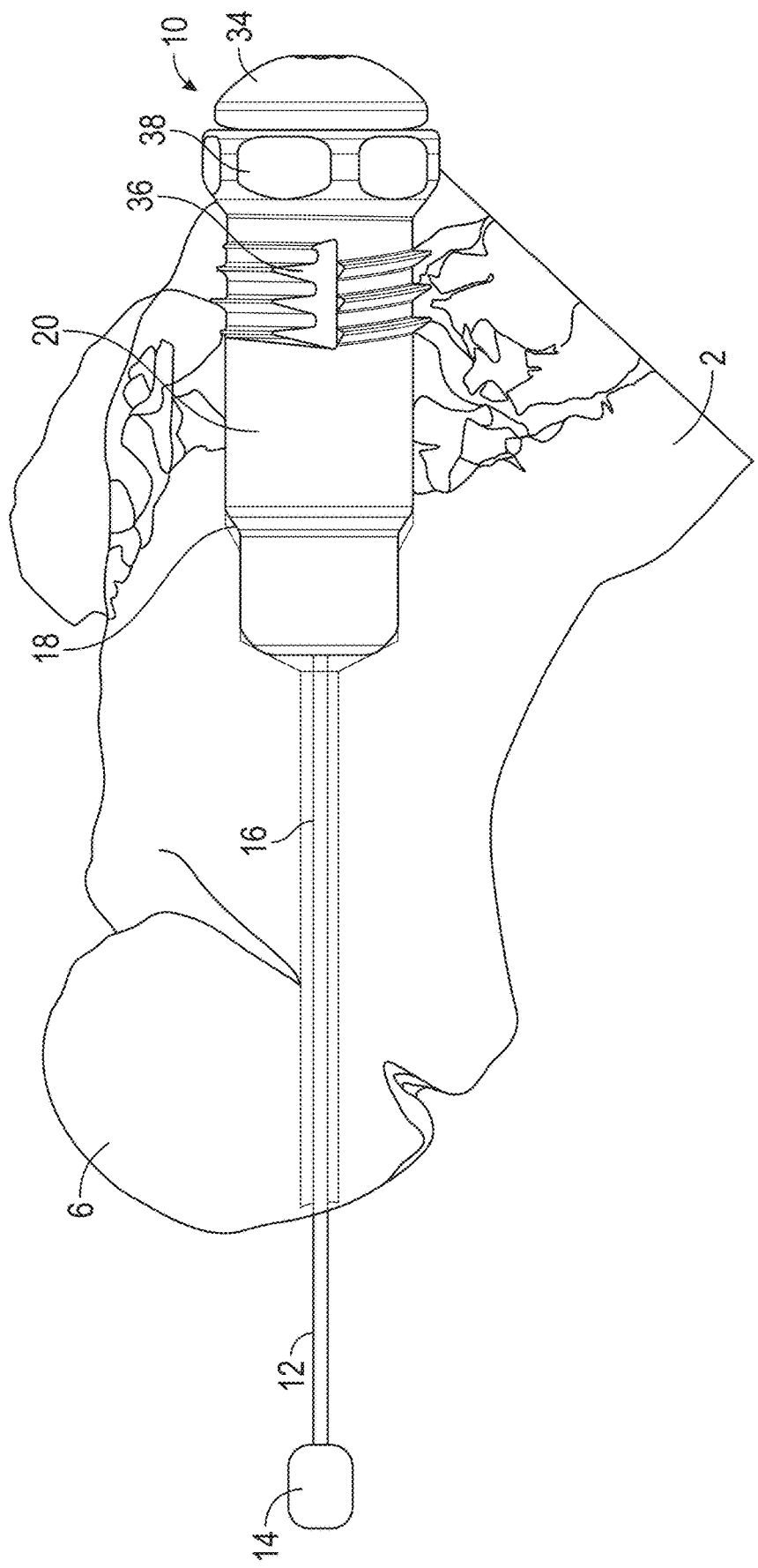
FIG. 2 shows the device of FIG. 1 implanted in a femur.
Figure 3:
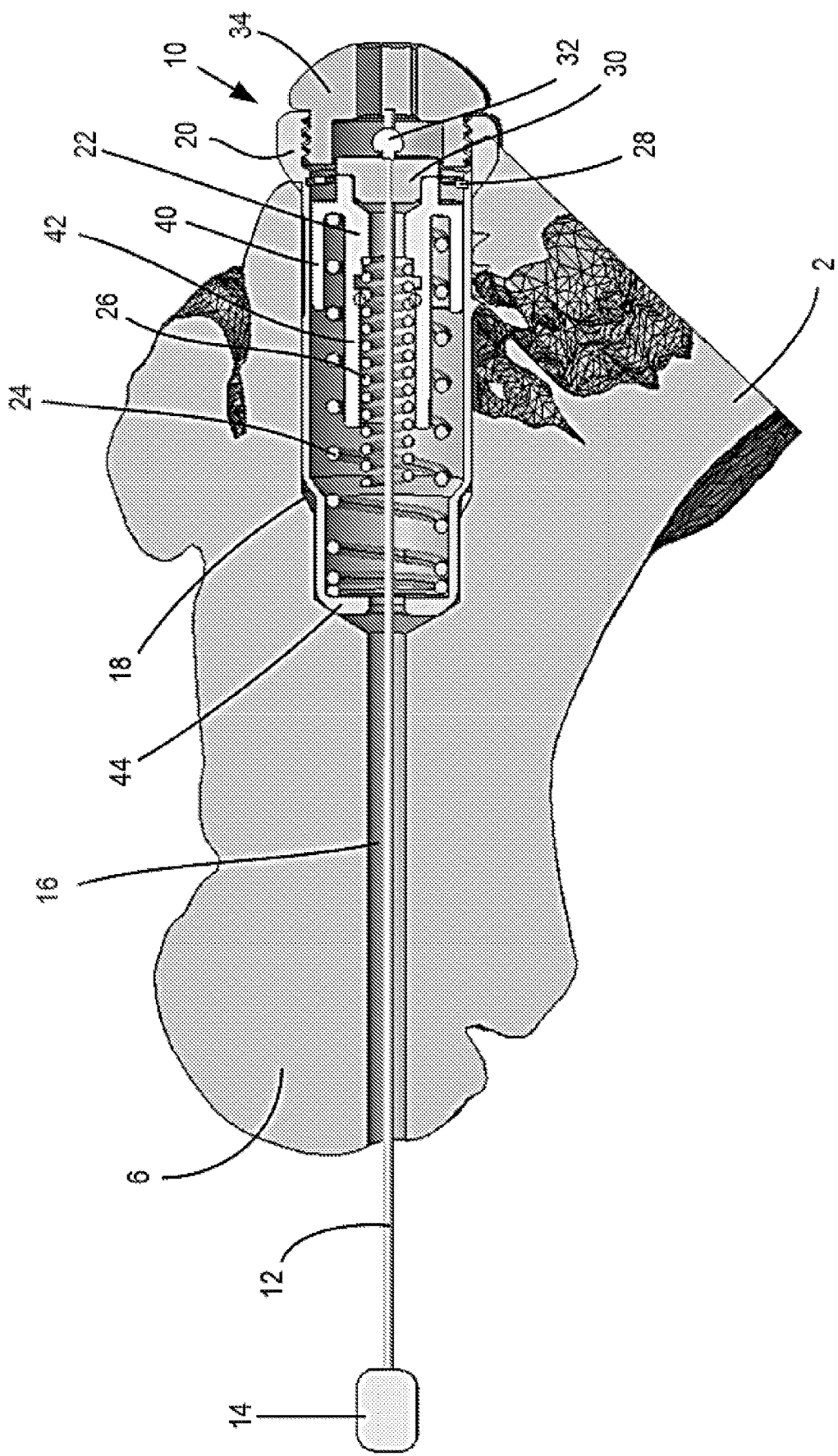
FIG. 3 is a cross-sectional view of FIG. 2.
Figure 5:
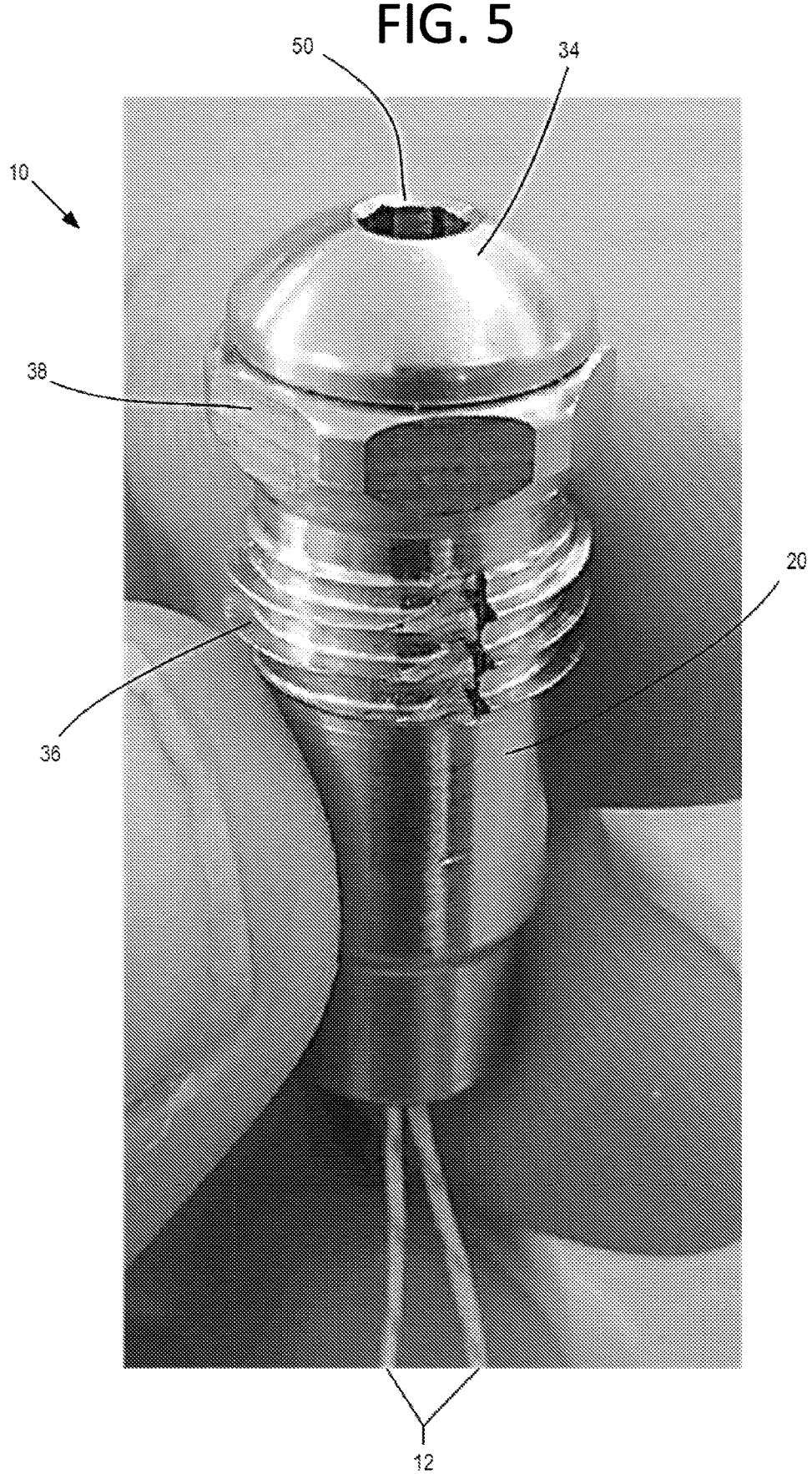
FIG. 5 is an enlarged view of the device of FIG. 4.
Figure 6:
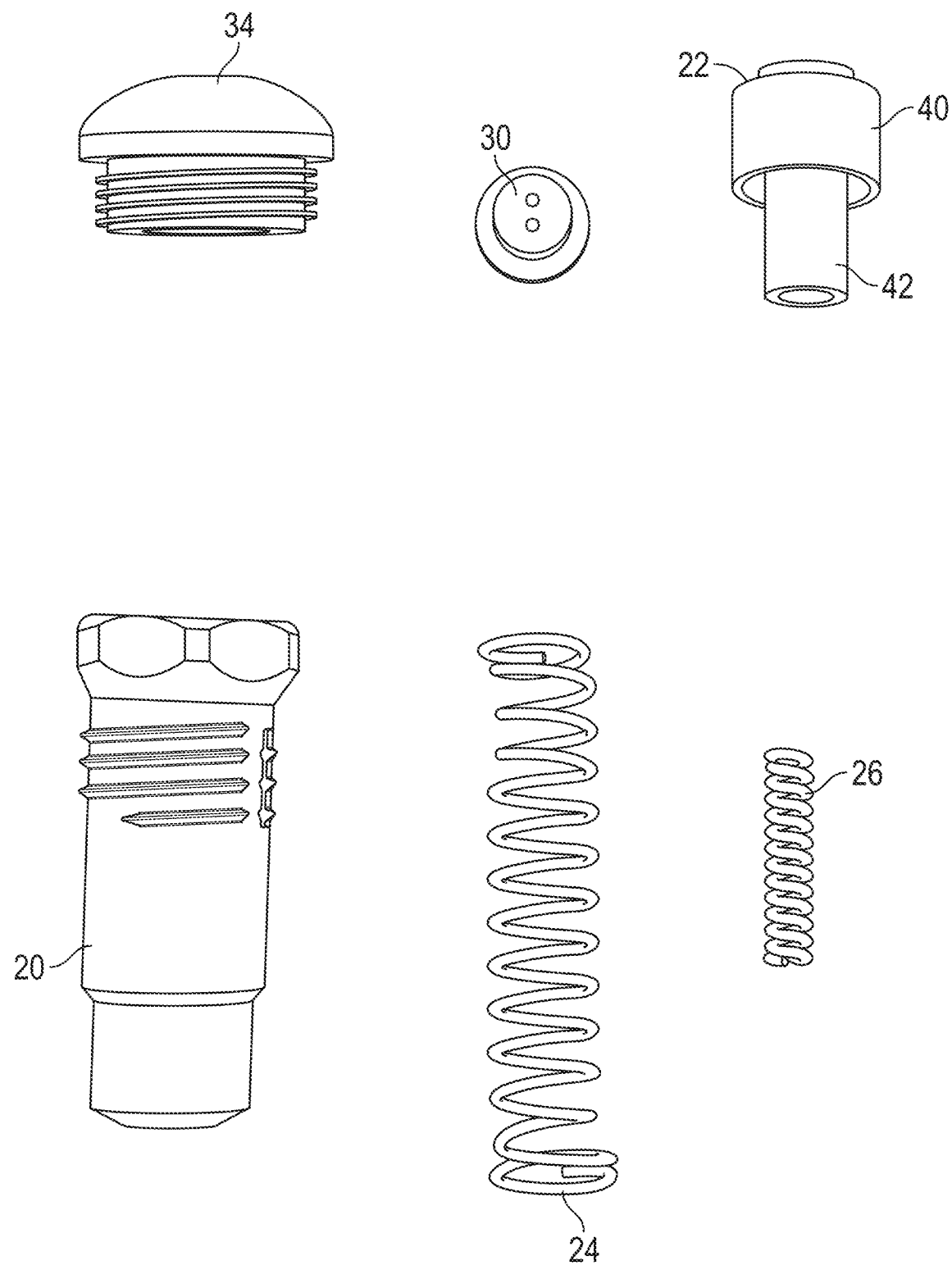
FIG. 6 shows the device of FIG. 4 disassembled.

FIGS. 2 and 3 show the top end of the femur 2 with the device 10 implanted in a cavity 18 near the greater trochanter region and the tether 12 passing through a tunnel 16 in the femoral head 6. As shown in FIGS. 3 and 6, the device 10 can comprise an outer housing 20, inner slider 22, a primary spring 24, a secondary spring 26, a retainer 28, a tether button 30, a tether securement device 32, and a cover 34. As shown in FIGS. 2 and 5, the outside of the housing 20 can include threads that act as a bone screw, such that the housing can be implanted by rotation of the housing to cause the threads to screw into the cavity 18 formed in the femur. A hex head 38, or the like, can be included on the rear of the housing 20 to allow a torque to be applied for screwing the housing into the cavity 18. In some embodiments, the housing 20 can comprise more than one part installed separately, such as a first part with outer threads installed first in the bone, and an inner second part that extends through and fixes to the inside of the first part.

Figure 7:
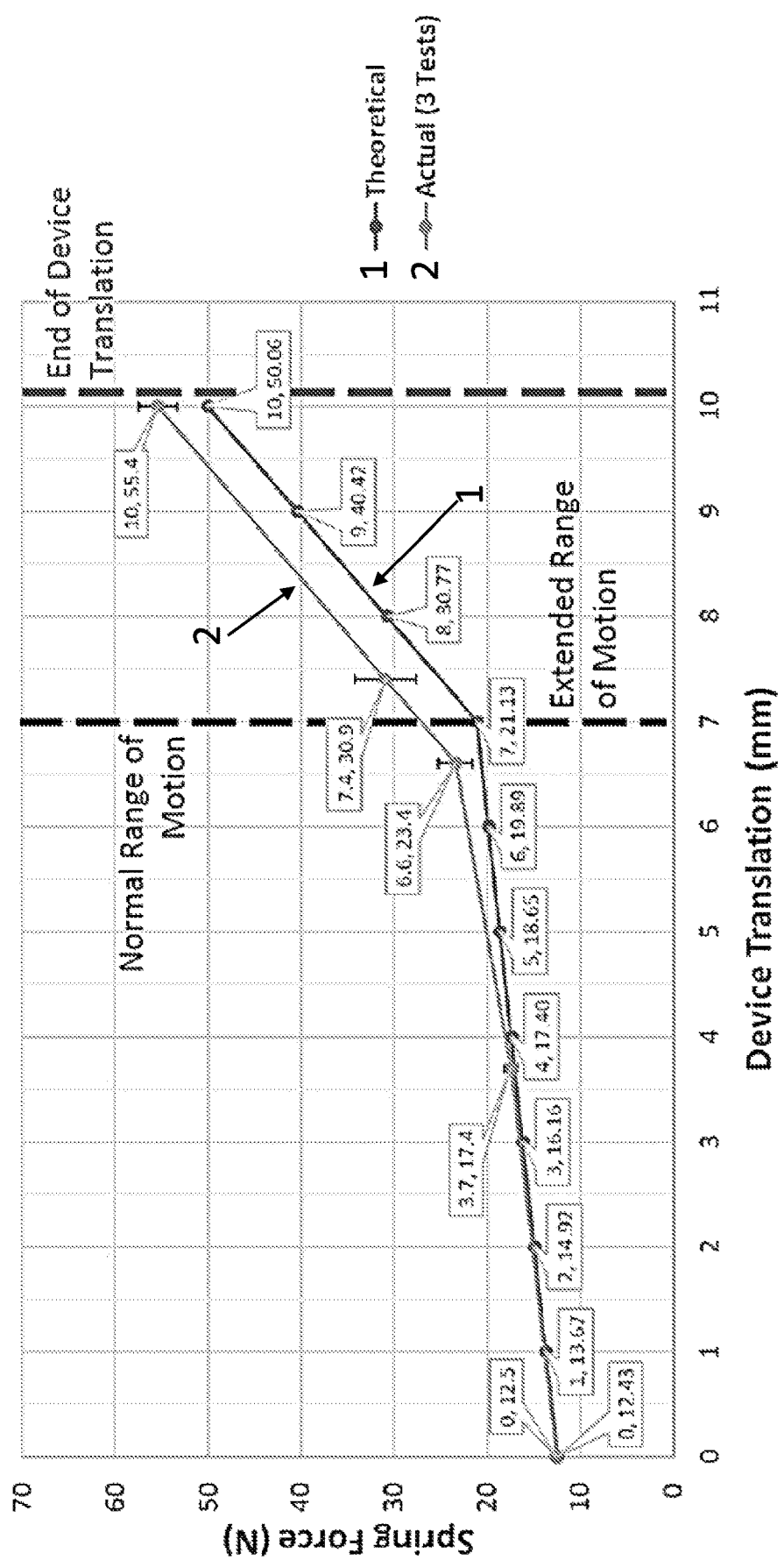
FIG. 7 is a graph illustrating the tension force applied by the hip joint tether device as a function of device translation.

As shown in FIG. 3, the slider 22 can include an outer cylinder 40 that slides along the inside of the housing 20, and an inner cylinder 42. The primary spring 24 can have one end engaged with an end wall 44 of the housing and the opposite end engaged with the slider between the inner and outer cylinders. The secondary spring 26 can have one end positioned inside the inner cylinder and the other end extending out free, projecting toward the end wall 44. Using this compound or dual spring design, an initial travel of the slider toward the end wall of the housing only causes the primary spring 24 to compress. Once the slider moves far enough that that the free end of secondary spring 26 contacts the end wall, then further slider travel toward the end wall causes both springs to compress, increasing the rate of spring force growth per unit of slider travel. This is also illustrated in the graph of FIG. 7. In other embodiments, the secondary spring can have one end fixed at or near the end wall 44 and a free second end projecting toward the slider. In these embodiments, as the primary spring compresses, the slider nears and eventually contacts the free end of the secondary spring, and further movement of the slider causes both springs to compress.

Figure 4:
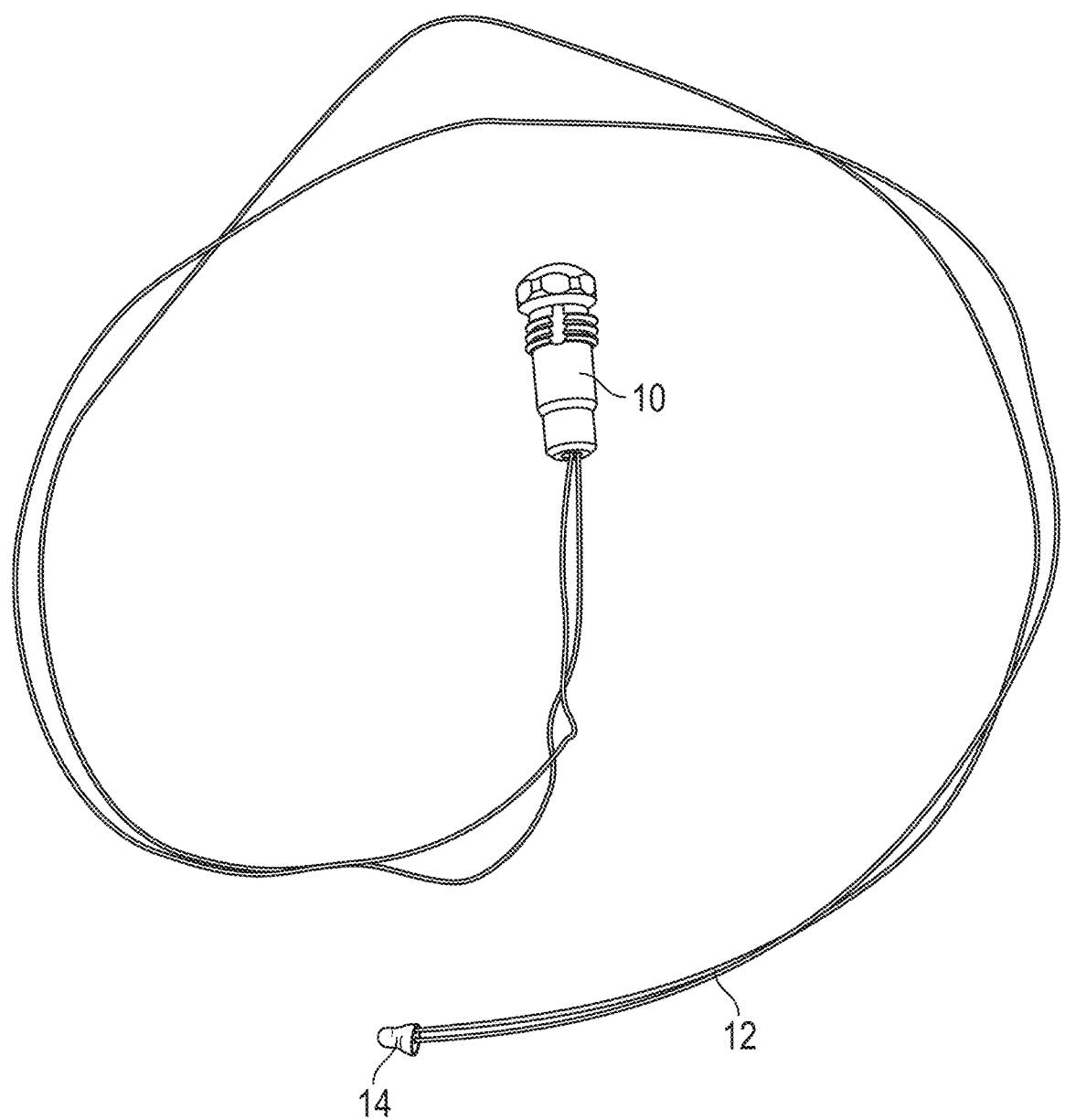
FIG. 4 shows an exemplary hip joint tether device in isolation.

The retainer 28 is coupled to the housing 20 behind the slider 22 to prevent the slider from inadvertently sliding out of the housing. The button 30 is seated behind the slider and has one or more openings to allow the tether to pass through the button and be secured to the back side of the button. The tether can comprise one, two, or more strands of material, such as suture, cords, wires, and the like. In the example of FIG. 4, the tether 12 includes two strands. Note that the length of the tether is exaggerated in FIG. 4. The tether 12 may be initially extra long prior to implantation, and then after the tether is tightened and secured to the implant device, excess tether length can be trimmed off. The implanted tether may be 30 mm to 100 mm in length, such as 40 mm to 70 mm.

As shown in FIG. 3, the tether 12 can pass through an opening in the end wall 44 of the housing, through the springs, through a passageway in the slider, and through the opening(s) in the button 30. The tether can be preloaded with a desired tension by the surgeon and then tied or secured behind the button, such as with a knot, crimp, or other securement device like a clip or clamp. With the tether 12 secured, the cover 34 can be placed over the rear of the housing 22 to enclose the inner components and provide a smooth outer surface for healing with the natural surrounding tissue.

When the device 10 is implanted and the tether 12 is secured at both ends, the device can have a resting configuration where the hip joint is fully seated and the slider 22 is farthest from the end wall 44 (as shown in FIG. 3). In this resting state, the tether can still be under a preload tension where the primary spring is slightly compressed and the tether is prevented from having slack. FIG. 7 illustrates an example where preload tension from the spring force (at 0 mm device translation) is about 12.5 N. The slightly compressed primary spring 24 urges the slider 22 and button 30 away from the end wall 44, and that spring force is transferred from the button to the tether 12. When the femoral head 6 begins to move away from the hip socket, the housing 20 moves with the femur 2 while the slider 22 and button 30 remain a constant distance from the tether anchor 14 location in the hip socket, which causes the end wall 44 of the housing to move closer to the slider, which compresses the primary spring 24. As the primary spring 24 compresses, the spring force it exerts increases linearly as a function of compression distance, increasing the tension on the tether, which pulls the femoral head back toward the hip socket with greater and greater force and the dislocation distance increases. In the example of FIG. 7, the primary spring force increases from about 12.5 N to about 23.4 N over the initial 6.6 mm of compression. The spring constant can be selected to provide a desire spring force profile as desired on a patient by patient basis.

In some embodiments, only a single spring is included, such as the primary spring 24. In some embodiments, a single spring can comprise a compound spring that provides a non-linear force-distance profile, such as by having some of the coils of the spring weaker than other coils. In the embodiment illustrated, two separate springs are included. The secondary spring 26 has a free end that initially is not engaged until the primary spring compresses a certain distance. In this example, the secondary spring engages the end wall 44 once the primary spring compresses around 7 mm. After that, the secondary spring begins to compress as well and the combined spring force of the two spring increases as a higher rate per unit of compression. In the example of FIG. 7, the spring force rapidly increases from 23.4 N to 55.4 N over 3.4 mm of compression from 6.6 mm to 10 mm of total compression of the primary spring.

The 0 mm to 7 mm range of spring compression can be selected to correspond with a "normal" range of motion for the patient's hip. Under this normal range of motion, a relatively low amount of tension is applied by the tether and more freedom is allowed in the hip joint. However, any motion that causes the femoral head to displace more than 7 mm from the resting position in the socket can be termed "extended" range of motion which is allowed but more dangerous and riskier to the hip joint. According, a higher level of tension is applied by the tether to more strongly urge the joint to move back to the normal range of motion. A maximum device translation distance can also be set, such as about 10 mm in the example of FIG. 7. This maximum can be set by contact between the slider 22 and the end wall 44, by the full compression length of either spring, or some other blocking mechanism that stops the slider from moving any closer toward the end wall. The maximum distance can be selected to correspond to an amount of hip displacement that is known to be a high risk of injury to the patient, for example.

The hip tethering devices disclosed herein can be scaled and sized as desired to accommodate various patient anatomies and conditions. For example, smaller sized devices can be used with infants, and larger sized devices can be used with older children or adults. For an exemplary 3 year old patient, with a femoral head diameter of about 20 mm, the implanted tether device can have an outer diameter of about 3 mm to 12 mm, such as from 5 mm to 10 mm, and the depth of the implant bore in to the bone can be 10 mm to 40 mm, such as about 20 mm to about 30 mm. Part of the implanted device can extend out beyond the bone bore, such as about 10 mm beyond outside of the bone. Thus, the implant can have an overall length (not including the tether itself) of 10 mm to 50 mm, such as about 20 mm to about 40 mm. The channel formed in the femoral head that allows passage of the tether can have a smaller diameter, such as 1 mm to 3 mm.

The disclosed technology can be implemented in conjunction with other hip joint tightening procedures. In some of hip joint procedures, the hip joint capsule is surgically tightened to help it better retain the femoral head. In some procedures, excess tissues (e.g., torn ligaments, fatty tissues) can be initially removed from the hip joint. In some procedures, the femur is surgically modified to change the angle, shape, and/or size of the femoral head to provide proper alignment, seating, and range of motion in the hip socket. In some of these procedures, a metal plate can be surgically attached to the femur to hold it in a desired position while it heals. The disclosed hip tether device can be used in conjunction with such a metal plate. For example, the housing 22 or other portions of the tether device may be secured to or integrated with such a metal plate, and implanted at the same time.

In some of procedures, a cast is placed on the patient after the surgery to hold the hip joint and leg in a desired position and reduce hip motion during healing. The disclosed hip tether device can be used in conjunction with and augment a cast to restrict unwanted motion of the hip during healing, or the hip tether device can replace the functionality of a cast and allow the patient to avoid some of the unwanted restrictions imposed by a cast.

The tether itself can comprise any suitable material, such any suture material, polymeric materials, natural/anatomic materials, metallic materials, fibrous materials, etc. The tether may comprise any number of strands of material as well, such a one strand, two strands, three strands, etc. The tether can be flexible but capable of holding a necessary about of tension. In some embodiments, the tether can elongate to a small degree under tension, but the tether can maintain close to the same fixed length between the first anchor point in the hip and the second anchor point behind the button 30. The flexibility of the tether allows the femur to articulate and rotate relative to the hip, while the device 10 allows only a safe degree of femur displacement from the hip.

In some embodiments, the tether can be re-tensioned after the initial implantation procedure. For example, if is found that the tether is too tight a few weeks after implantation, and the patient's hip is too restricted, then the cover 34 may be accessed and removed and the inner components of the implanted device can be adjusted to change the tension profile. This can be done by changing the length or size of the springs, changing the placement of the slider/button, and/or changing the length or tightness of the tether itself. Once adjusted, the cover can be replaced. The implant's position at the lateral aspect of the femur makes for relatively easy surgical access compared to accessing the hip joint itself.

The tether may be dissolvable over time, or may be permanent, or may be surgically removable at a later date. In some embodiments, the hip tether device is configured to stay in a patient for certain period of time (e.g., 3-12 months) and then the device can be surgically removed from the patient. For example, after a sufficient time has passed, the tether may have dissolved leaving the implanted device ready to be removed. With the tether dissolved, the device can be removed by simply rotating the housing to unscrew the housing from the bone, with the springs and other components contained inside the housing and cover. Alternatively, the cover can be removed first and the internal components can be removed from inside the housing, and the housing can be unscrewed from the bone last. After removal, the empty bores in the femur can be filled to reinforce the bone again. Similarly, the tether anchor in the hip bone may be surgically removed or left in permanently.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein, or in the references incorporated by reference herein, unless incompatible therewith. All of the features disclosed in this specification (including any accompanying claims, abstract and drawings) and in the incorporated references, and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings) and incorporated references, or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the included figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims and their equivalents.

The invention claimed is:

1. A dynamic hip tethering device, comprising:
   a femoral implant comprising:
      a housing that is configured to anchor the femoral implant to the femur;
      a primary spring and a secondary spring disposed within the housing; and
      a slider coupled to the primary spring and the secondary spring, such that the slider can move relative to the housing via compression and expansion of the primary spring; and
   a tether having a first end and a second end, wherein the first end is configured to anchor at or near a patient's acetabulum, the tether is configured to pass through the patient's femoral head, and the second end couples to the slider of the femoral implant, such that the tether is configured to span across the patient's hip joint;
   wherein the implant is configured such that relative motion between the slider and the housing allows a limited degree of separation of the femoral head from the acetabulum, while the primary spring applies a variable tension load to the tether that is configured to resist separation of the femoral head from the acetabulum when implanted into the patient;
   wherein the primary spring is always engaged between the housing and the slider, and wherein the secondary spring is only engaged between the housing and the slider when the primary spring is compressed at least a predetermined distance, wherein when the secondary spring is engaged, it applies a variable tension load to the tether that is configured to resist separation of the femoral head from the acetabulum.

2. The device of claim 1, wherein the primary spring and the secondary spring comprise a compound spring.

3. The device of claim 1, wherein the primary spring and the secondary spring are configured such that the variable tension load increases as a function of the degree of separation of the femoral head from the acetabulum.

4. The device of claim 1, wherein the femoral implant is configured to be implanted in a greater trochanter region of the femur.

5. The device of claim 1, wherein the tether comprises two or more strands.

6. The device of claim 1, wherein the tether is bioresorbable.

7. The device of claim 1, wherein the tether passes through an opening in an end wall of the housing, through the slider, and is secured to a button or washer positioned behind the slider within the housing.

8. The device of claim 1, wherein the femoral implant further comprises a cover that is configured to be exposed outside of the femur, wherein the cover is securable to the housing to enclose the slider and the primary spring and the secondary spring.

9. The device of claim 1, wherein the slider comprises an inner cylinder and an outer cylinder, wherein the inner cylinder is coupled to the outer cylinder and the outer cylinder is disposed radially outward from the inner cylinder.

10. The device of claim 9, wherein the primary spring is at least partially disposed between the inner cylinder and the outer cylinder.

11. The device of claim 9, wherein the secondary spring is at least partially disposed within the inner cylinder.

12. A method of implanting a dynamic hip tethering device, comprising:

anchoring a first end of a tether at or near a patient's acetabulum;

implanting a femoral implant in the patient's femur adjacent its femoral head;

passing the tether through the femoral implant and coupling a second end of the tether to a slider of the femoral implant, such that the tether spans across the patient's hip joint, the tether being under a first non-zero tension when the patient's hip joint is not separated, and the first non-zero tension resisting separation of the hip joint, wherein the slider is coupled to a spring of the femoral implant such that the slider can move relative to a housing of the femoral implant that is engaged with the femur and is configured to travel a maximum distance relative to the housing to allow the femoral head to separate the maximum distance from the acetabulum, and wherein when the hip joint is separated the maximum distance the tether is under a second non-zero tension that is greater than the first non-zero tension.

13. The method of claim 12, further comprising inducing relative motion between the slider and the housing to cause separation of the patient's femoral head from the acetabulum while the spring compresses and applies a tension load to the tether that resists separation of the femur head from the acetabulum.

14. The method of claim 12, wherein implanting the femoral implant comprises implanting the femoral implant in a greater trochanter region of the femur.

15. The method of claim 12, wherein anchoring the first end of the tether comprises passing the tether through an opening in the acetabulum.

16. The method of claim 12, wherein coupling the second end of the tether to the slider comprises passing the tether through the slider and securing the second end of the tether to a button or washer positioned behind the slider within the housing.

17. The method of claim 12, further comprising attaching a cover to the housing that covers the slider, such that the slider and the second end of the tether are contained inside the housing.

18. The method of claim 12, wherein implanting the femoral implant comprises rotating the housing such that threads on the housing engage with the femur.

19. The method of claim 12, further comprising re-tensioning the tether after an initial implantation procedure to adjust tension in the tether.

* * * * *